| United States Patent [19] | [11] 4,455,375 |
|---|---|
| Schneider et al. | [45] Jun. 19, 1984 |

[54] STABILIZED RENNET SOLUTION

[75] Inventors: Palle Schneider, Ballerup; Sven Branner-Jørgensen, Charlottenlund, both of Denmark

[73] Assignee: Novo Industri A/S, Denmark

[21] Appl. No.: 417,856

[22] Filed: Sep. 14, 1982

[30] Foreign Application Priority Data

Sep. 21, 1981 [DK] Denmark .............................. 4168/81

[51] Int. Cl.³ .......................... C12N 9/96; C12N 9/58
[52] U.S. Cl. ..................................... 435/188; 435/223
[58] Field of Search ........................ 435/188, 223, 226

[56] References Cited

U.S. PATENT DOCUMENTS

| 3,051,627 | 8/1962 | Bradford et al. | 435/188 |
| 3,950,513 | 4/1976 | Jensen | 435/188 X |
| 4,255,454 | 3/1981 | Branner-Jorgensen | 435/223 X |
| 4,348,482 | 9/1982 | Cornelius | 435/223 |

Primary Examiner—Lionel M. Shapiro
Attorney, Agent, or Firm—Fidelman, Wolffe & Waldron

[57] ABSTRACT

A stabilized solution of rennet; the stabilizing agent being methionine. The stabilizing agent is added in an amount corresponding to a concentration of between 0.1% (w/w) and saturation calculated on the total weight of the solution.

7 Claims, 1 Drawing Figure

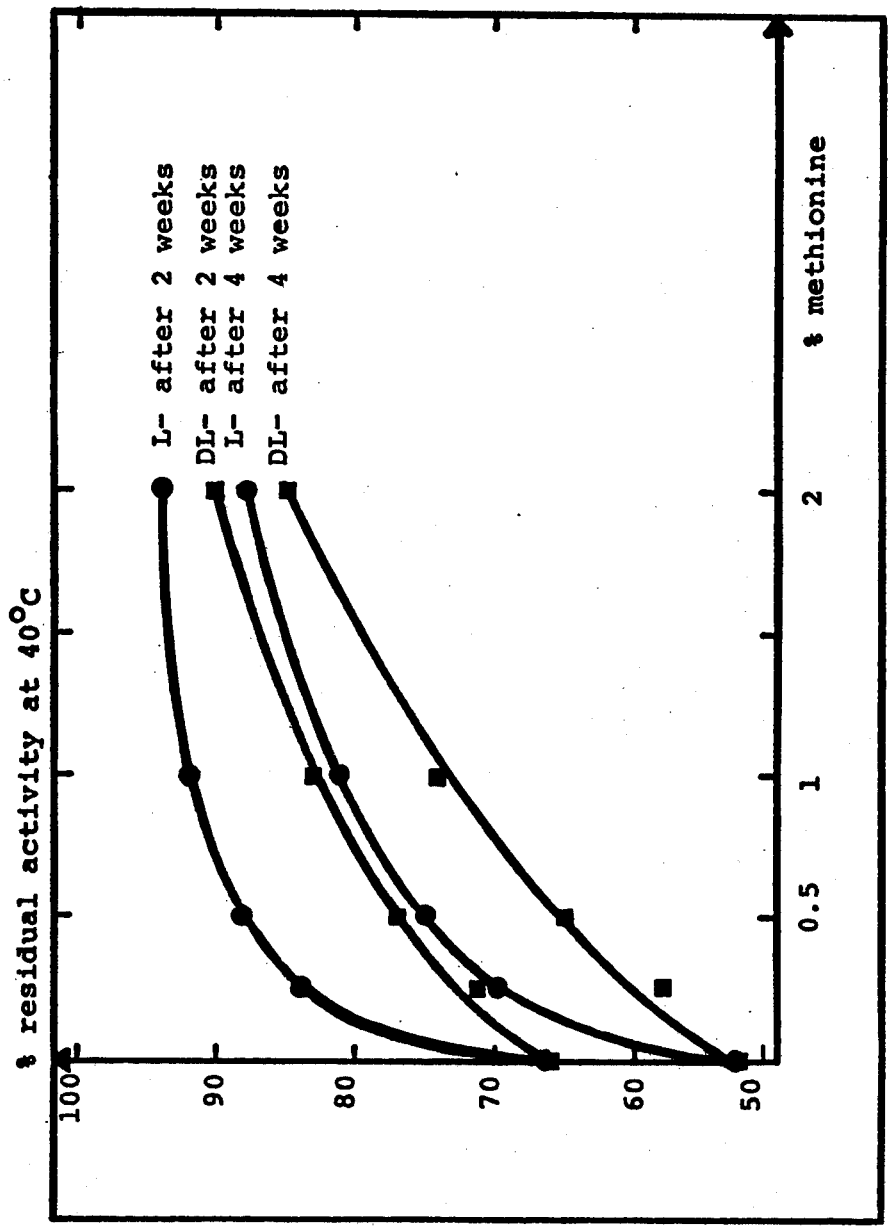

STABILIZED RENNET SOLUTION

BACKGROUND OF THE INVENTION

For ease of dosing, rennet is most frequently marketed in solution form. In general, however, rennet solutions are not as stable as rennet powder, in regard to rennet activity, especially when subjected to elevated storage temperatures. As might be expected under these circumstances, addition of stabilizing agents to the rennet solution in order to improve the stability has been suggested to the art. Sorbitol has been commercially used for stabilizing agent, usually in an amount of around 50% (w/w) calculated on the solution.

Most, but not all, of any stabilizing agent added to a rennet solution will be taken up by the whey phase. However, since some small part will be taken up by the curd phase, some of the stabilizing agent will be present ultimately in the cheese. For reason that it is a foreign material, the presence of sorbitol in the cheese is most undesirable and, as a matter of fact, sorbitol is not approved in some countries for stabilization of rennet. Further, sorbitol is a relatively expensive material, and because around 50% of sorbitol has to be added in order to obtain a reasonable stabilization, the price of the stabilized rennet solution is considerably higher than that of the unstabilized rennet solution.

Thus, a need exists for a stabilized solution of rennet, wherein the stabilizing agent would not be considered a foreign substance, and wherein inclusion of the stabilizing agent does not add very much to the price of the rennet solution.

The present invention is based upon discovery that small amounts of methionine exhibits a strongly stabilizing effect on the enzymatic activity of a rennet solution.

SUMMARY OF THE INVENTION

According to the invention a stabilized solution of rennet is provided, wherein the stabilizing agent is methionine added in an amount corresponding to a concentration of between 0.1% (w/w) calculated on the total weight of the solution and that of a rennet solution saturated with methionine.

In a preferred embodiment of the present invention the methionine is added in an amount corresponding to a concentration of between 0.2% (w/w) and saturation calculated on the total weight of the solution.

The rennet activity in the solution of rennet is at least 5,000 RU/ml and preferably at least 10,000 RU/ml.

The rennet activity indicated in RU/ml (RU=Rennet Units) is measured according to British Standard 3624:1963 (Method for the determination of the milk coagulating power of rennet).

A rennet solution saturated with respect to methionine is normally a 2-3% (w/w) solution, the maximum methionine content depending on the other constituents present in the solution and on the temperature. In case the methionine is added to rennet which has been thermally destabilized by treatment with an oxidant, any residual destabilizing agent would react with the methionine and as a consequence more than 3% methionine might be needed to obtain a saturated solution.

As will be apparent from the examples herein provided methionine is used in such small amounts as compared with sorbitol that a substantial reduction of the cost for stabilizing rennet solutions is obtained.

Methionine is preferably added in an amount corresponding to a concentration of between 0.1 and 2% (w/w) and more preferably between 0.5 and 1.5% (w/w) calculated on the total weight of the rennet solution.

As methionine is an essential amino acid already contained in cheese, no foreign substance is introduced in the cheese by the use of methionine as a stabilizing agent. Further, only a minor amount of methionine is added compared to what is already contained in the cheese.

The disclosures of U.S. Pat. No. 3,051,627 and British Pat. No. 866,423 teach that methionine along with a group of different amino acids can be used as a stabilizing agent for solutions of chymotrypsin, advising that all the amino acids tested (including D,L-methionine) exhibit substantially the same stabilizing effect. Also, according to British Pat. No. 900,115 D,L-methionine and other amino acids can be used as stabilizing agent for trypsin solutions.

Therefore, it is believed to be quite surprising that methionine appears to be the only amino acid effective for stabilizing rennet from among a large number of amino acids.

A preferred embodiment of the stabilized solution of rennet according to the invention comprises use of methionine in its D,L-form.

Another preferred embodiment of the stabilized solution of rennet according to the invention comprises use of methionine in its L-form.

A further preferred embodiment of the stabilized solution of rennet according to the invention is microbial rennet. As microbial rennets, the following can be mentioned: *Mucor miehei* rennet, *Mucor pusillus* rennet, and *Endothia parasitica* rennet; a preferred embodiment of the stabilized solution of rennet according to the invention comprises the microbial rennet derived from *Mucor miehei*.

Another preferred embodiment of the stabilized solution of rennet according to the invention comprises rennet derived from thermally destabilized *Mucor miehei* rennet.

Another preferred embodiment of the stabilized solution of rennet according to the invention comprises *Mucor miehei* rennet thermally destabilized by treatment with an oxidizing agent according to practice of U.S. Pat. No. 4,255,454 or Belgium Pat. Nos. 882689 or 882690.

If an oxidizing agent is employed for the thermal destabilizing agent, stabilization according to practice of the present invention is particularly advantageous since methionine, being a reduction agent, would reduce any remaining (small) residues of the oxidizing agent in the rennet solution and thereby remove such unwanted constituents.

DETAILED DESCRIPTION OF THE INVENTION

Methionine is normally added at one of the final recovery steps in the preparation of the microbial rennet. If the microbial rennet is thermally destabilized with an oxidizing agent, the methionine must be added after the destabilizing process.

The content of active enzyme in the rennet solutions is adjusted to 0.25-3% (w/w), for instance by addition of a sodium chloride solution.

The hereto attached drawing illustrates the residual activity of a *Mucor miehei* rennet (Rennilase 50 L type TL) at 40° C. after 2 and 4 weeks. The stabilizing effect of L-methionine is greater than that of D,L-methionine, especially at lower concentrations.

For further understanding of the invention, the following examples are provided:

EXAMPLE 1

The rennet preparation used for this experiment was a commercial destabilized *Mucor miehei* rennet (Rennilase 50 L type TL) manufactured according to Example 3 (dose approximately 1.6% v/v 2.25M NaOCl) in Belgium Pat. No. 882689. (See also U.S. patent application Ser. No. 096,213, now U.S. Pat. No. 4,357,357.)

This preparation is standardized with a 18% w/w sodium choride solution to a content of approximately 1% active enzyme.

Two batches of the Rennilase 50 L type TL were tested for storage stability at pH 6.5, the tests being conducted with a reference sample without any stabilizing agent and a sample with 1% w/w D,L-methionine. The storage stability tests have been performed as a "normal" stability test at 25° C. and as an accelerated test at 40° C. The test results appear in the following table.

TABLE I

| Incubation temperature | Percent residual activity | | |
|---|---|---|---|
| | 25° C. | | 40° C. |
| Incubation time | 4 weeks | 18¼ weeks | 2 weeks |
| Batch PRN 4519 reference, without stabilizer | 95.3 | 81.3 | 74.3 |
| Batch PRN 4519 with 1% D,L-methionine | 102.0 | 97.9 | 89.5 |
| Batch PRN 4520 reference, without stabilizer | 97.1 | 81.0 | 75.5 |
| Batch PRN 4520 with 1% D,L-methionine | 102.8 | 94.4 | 88.4 |

EXAMPLE 2

In order to compare the stabilizing effect of methionine with that of some other amino acids 1% w/w of different amino acids were added samples of a Rennilase 50 L type TL (batch PRN 4518 prepared as in Example 1). A sample without any addition of amino acid was tested as a reference. All samples were adjusted to pH 6.5. The samples were stored at 40° C. for 2 weeks and residual activities were determined, vide Table II.

TABLE II

| Rennilase 50 L type TL | Percent residual activity after 2 weeks at 40° C. |
|---|---|
| Reference without amino acid added | 69.8 |
| With 1% D,L-methionine | 88.1 |
| With 1% L-asparagine | 72.2 |
| With 1% L-histidine, HCl | 74.5 |
| With 1% L-arginine | 74.1 |
| With 1% L-lysine | 72.0 |
| With 1% L-Na—glutaminate | 71.7 |

It appears from the test results tabulated above that only methionine provides an effective stabilization for the rennet preparation.

EXAMPLE 3

The stabilizing effect of methionine was compared with that of glycine and alanine. 2% w/w of the amino acid was added to samples of a Rennilase 50 L type TL (batch PRN 4516 prepared as in Example 1). As reference a sample without any addition of amino acids was used. All samples were adjusted to pH 6.5 and stored at 40° C. for 2 weeks. Residual activities found are listed in the following table:

TABLE III

| Rennilase 50 L type TL | Percent residual activity after 2 weeks at 40° C. |
|---|---|
| Reference without amino acid added | 74 |
| With 2% D,L-methionine | 96 |
| With 2% glycine | 77 |
| With 2% D,L-alanine | 78 |

EXAMPLE 4

The stabilizing effect of D,L-methionine was compared with that of L-methionine. In addition, the effect of a methionine derivative, i.e., D,L-methionine sulphoxide, and of still another amino acid, i.e., L-cystein, were investigated. Varying proportions of the amino acid was added to samples of Rennilase 50 L typr TL (mixed batches of equal parts of PRN 4526, PRN 4527, and PRN 4528). A sample without addition of amino acid was used as reference. All samples were adjusted to pH 6.5 and stored at 40° C. for 2 and 4 weeks and at 25° C. for 26 weeks. The test details and test results are provided in the following table:

TABLE IV

| Rennilase 50 L type TL | Percent residual activity | | |
|---|---|---|---|
| Incubation temperature | 25° C. | 40° C. | |
| Incubation time | 26 weeks | 2 weeks | 4 weeks |
| Ref. without amino acid added | 63 | 66 | 53 |
| With 0.25% D,L-methionine | 70 | 71 | 58 |
| With 0.50% D,L-methionine | 76 | 77 | 65 |
| With 1.0% D,L-methionine | 84 | 83 | 74 |
| With 2.0% D,L-methionine | 90 | 90 | 85 |
| With 0.25% L-methionine | 78 | 84 | 70 |
| With 0.50% L-methionine | 83 | 88 | 75 |
| With 1.0% L-methionine | 89 | 92 | 81 |
| With 2.0% L-methionine | 96 | 94 | 81 |
| With 1.0% D,L-methionine sulphoxide | 67 | 74 | 60 |
| With 2.0% L-cysteine | 60 | 67 | 57 |

It appears from the data tabulated above that L-methionine provides a better stabilization of the rennet preparation than the D,L-methionine. L-cysteine has no effect, and D,L-methionine sulphoxide only a minor effect on the stability.

EXAMPLE 5

The stabilizing effect of D,L-methionine was tested in a 10% w/w/ solution of a commercial *Mucor pusillus* rennet, Nourylab 1:220,000 (Charge No. 75 I 1-22) with 18% w/w/ sodium chloride added for preservation; the pH of the samples was adjusted to pH 4.7. A reference sample and a sample with 1% D,L-methionine were incubated at 40° C., 25° C., and 4° C. and residual coagulating activities were determined.

TABLE V

| 10% w/w Nourylab Incubation temp. | Percent residual activity | | | | |
|---|---|---|---|---|---|
| | 40° C. | | 25° C. | | 4° C. |
| Incubation time | 2 weeks | 4 weeks | 4 weeks | 4 weeks | 26 weeks |
| Reference without amino acid added | 34 | 25 | 55 | 93 | 76 |
| With 1% D,L- | 51 | 39 | 73 | 96 | 88 |

TABLE V-continued

| 10% w/w Nourylab | Percent residual activity | | | |
|---|---|---|---|---|
| Incubation temp. | 40° C. | | 25° C. | 4° C. |
| Incubation time | 2 weeks | 4 weeks | 4 weeks | 4 weeks | 26 weeks |
| methionine | | | | | |

It appears that D,L-methionine provides a substantial improvement in the storage stability of *Mucor pusillus* rennet.

EXAMPLE 6

The starting material for this Example was a rennet concentrate prepared as indicated in "2nd Pilot Plant Experiment" in British Pat. No. 1,108,287, only the culture liquid was concentrated to an activity corresponding to approximately 1% solution of the pure enzyme.

This material was further purified and concentrated by precipitation with 40% w/vol ammonium sulphate and washing with tap water during a subsequently performed ultrafiltration. The resultant rennet concentrate (batch PRB 1031) contained approximately 4% active enzyme after addition of 18% w/w sodium chloride for preservation.

The stability test with 1% and 2% of D,L-methionine and reference sample was performed at 40° C. and pH 6.8. The results are tabulated below.

TABLE VI

| Rennet concentrate PRB 1031 | Percent residual activity | | |
|---|---|---|---|
| | after 4 weeks | after 13 weeks | after 26 weeks |
| Reference without methionine | 88.1 | 72.1 | 59 |
| Test with 1% D,L-methionine | 98.8 | 88.7 | 80 |
| Test with 2% D,L-methionine | 98.9 | 92.1 | 84 |

We claim:
1. A stabilized solution of microbial rennet wherein the stabilizing agent is methionine in an amount corresponding between 0.1% (w/w) and saturation calculated on the total weight of the solution.
2. A stabilized solution of rennet according to claim 1 wherein methionine is between 0.2% (w/w) and saturation.
3. A stabilized solution of rennet according to claim 1 wherein methionine is between 0.5 and 1.5% (w/w).
4. A stabilized solution of rennet according to claim 1 wherein the methionine is D,L-methionine.
5. A stabilized solution of rennet according to claim 1 wherein the methionine is L-methionine.
6. A stabilized solution of rennet according to claim 1 wherein the rennet is *Mucor miehei* microbial rennet.
7. A stabilized solution of rennet according to claim 1 wherein the rennet is thermally destabilized *Mucor miehei* microbial rennet.